United States Patent [19]

Argoudelis et al.

[11] 4,368,193
[45] Jan. 11, 1983

[54] PROCESS FOR TREATING MALARIA

[75] Inventors: Alexander D. Argoudelis; David W. Stroman, both of Portage, Mich.

[73] Assignee: The Upjohn Company, Kalamazoo, Mich.

[21] Appl. No.: 255,541

[22] Filed: Apr. 20, 1981

[51] Int. Cl.³ .............................................. A61K 31/70
[52] U.S. Cl. .................................................. 424/180
[58] Field of Search ......................................... 424/180

[56] References Cited

U.S. PATENT DOCUMENTS

| | | | |
|---|---|---|---|
| 3,086,912 | 4/1963 | Bergy et al. | 424/180 |
| 3,496,163 | 2/1970 | Birkenmeyer et al. | 424/180 |
| 3,671,647 | 6/1972 | Argoudelis et al. | 424/180 |
| 4,278,789 | 7/1981 | Birkenmeyer | 424/180 |

*Primary Examiner*—Jerome D. Goldberg
*Attorney, Agent, or Firm*—Roman Saliwanchik

[57] ABSTRACT

A process for treating a protozoan disease, for example, malaria, by the systemic administration to a subject hosting a malarial parasite of the 3-(5'-ribonucleotide) of a novel analog of the well-known antibiotics lincomycin and clindamycin. The analogs are prepared by condensing a cyclic acid with a sugar amine. The 3-ribonucleotides of these analogs can be prepared by microbiological transformation procedures.

31 Claims, No Drawings

PROCESS FOR TREATING MALARIA

DESCRIPTION

1. Background of the Invention

The characteristics and preparation of the antibiotic lincomycin are disclosed in U.S. Pat. No. 3,086,912. Clindamycin is disclosed in U.S. Pat. No. 3,496,163. These antibiotics have been extensively used as medicines in humans and animals. A number of patents world-wide have issued concerning these antibiotics and a variety of derivatives thereof.

The structural formulas for lincomycin (1) and clindamycin (2) are shown in Chart 1.

Lincomycin and clindamycin 3-nucleotides are disclosed and claimed in U.S. Pat. No. 3,671,647. All of the lincomycin and clindamycin compounds disclosed in U.S. Pat. No. 3,671,647 have the propyl hygric acid moiety. These 3-nucleotides were found by test against S. aureus in vivo to have an activity approximately one-tenth of the parent compound.

2. Brief Summary of the Invention

This invention relates to the prophylactic and therapeutic treatment of subjects hosting a protozoan parasite by the systemic administration of the 3-nucleotides of the compounds shown in Chart 2 and Chart 3.

The lincomycin- and clindamycin-type compounds which can be converted to the 3-ribonucleotides are shown in Chart 2. In place of the hydroxyl at the three position of the lincosaminide moiety, there is substituted a nucleoside selected from the group consisting of adenylic acid, guanylic acid, cytidylic acid and uridylic acid.

The 3-ribonucleotides of the subject invention can be prepared by microbiological transformation procedures. The 3(-5'-ribonucleotides) obtained by transformation of U-57930 are shown in Chart 3.

DETAILED DESCRIPTION

It has been found in accordance with the present invention that the systemic administration of a compound of the formulas in Chart 2 and Chart 3 to a subject hosting a protozoan parasite provides effective suppressive treatment of the disease. For example, when the protozoan is a malarial parasite, the subject can be animal, e.g., mice infected with Plasmodium berghei; birds, e.g. ducks infected with P. lophurae and chicks infected with P. gallinaceum, and mammals such as primates, e.g., monkeys infected with P. cynomolgi, and humans infected with P. falciparum, P. vivax, and P. malariae.

Mammals hosting a parasitic protozoan of the class Sporozoa, order Coccidia (a microparasite producing the disease coccidiosis) can be treated by administration of the compounds of the present invention. For example cattle infected with Eimeria zurnii, E. bovis, E. ellipsoidalis; sheep and goats with E. parva, E. faurei; swine with E. debliecki, E. scabra, and Isospora suis; dogs and cats with Isospora bigemina, I. felis, E. canis, E. felina; poultry with E. tenella; rabbits with E. stiedae, E. perforans; and mink with E. mustelae can be treated.

The compounds of the formulas can be administered systemically by the oral and parenteral routes preferably in associated with a pharmaceutical carrier or in the case of animals (orally) in association with the animals feed. Additionally, the compounds of the formulas can be mixed with table salt for administration to humans for use in a program of mass drug administration in developing countries.

Advantageously, the compounds of the formulas do not exhibit cross-resistance when used against drug resistant, e.g., chloroquine or dimethyldiphenylsulfone (DDS), strains of malarial parasites.

The process of the present invention is accomplished by oral or parenteral administration of pharmaceutical compositions preferably presented for administration to humans and animals in unit dosage forms, such as tablets, capsules, pills, powders, granules, sterile parenteral solutions or suspensions, and oral solutions or suspensions, and oil-water emulsions containing suitable quantities of a compound of the formulas in the form of the free base, or its pharmacologically acceptable salts.

For oral administration, either solid or fluid unit dosage forms can be prepared. For preparing solid compositions such as tablets, the principle active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or a mixture of polymeric acids with such materials as shellac, cetyl alcohol, cellulose acetate, phthalate, styrene maleic acid copolymer and the like. Alternatively, the two component system can be utlized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the compound of the formulation with an inert pharmaceutical diluent and filling the mixture into a hard gelatin capsule of appropriate size. In another embodiment, capsules are prepared by filling hard gelatin capsules with polymeric acid coated beads containing a compound of the formulas. Soft gelatin capsules are prepared by machine encapsulation of a slurry of a compound of the formulas with an acceptable vegetable oil, light liquid petrolatum or other inert oil.

Fluid unit dosage forms for oral adminstration such as syrups, elixirs, and suspensions can be prepared. The water-soluble forms of a compouond of the formulas can be dissolved in an aqueous vehicle together with sugar, aromatic flavoring agents and preservatives to form a syrup. An elixir is prepared by using a hydroalcoholic (ethanol) vehicle with suitable sweeteners such as sucrose together with an aromatic flavoring agent. Suspensions can be prepared of the insoluble forms with a syrup vehicle with the aid of a suspending agent such as acacia, tragacanth, methylcellulose, and the like.

For parenteral administration, fluid unit dosage forms are prepared utilizing a compound of the formulas and a sterile vehicle, water being preferred. The compound, depending on the form and concentration used, can be either suspended or dissolved in the vehicle. In preparing solutions, a water-soluble form of a compound of the formulas can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the powder prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. For sustained action, an intramuscular suspension is prepared with an insoluble form such as the trimethylsilyl ether or the pamoate salt. Advantageously, a surfactant or wetting agent is included in the composition to facilitate uniform distribution of the compound.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, pills, troches, suppositories, powder packets, granules, wafers, cachets, teaspoonfuls, tablespoonfuls, dropperfuls, ampuls, vials, segregated multiples of any of the foregoing, and other forms as herein described.

In addition to the administration of a compound of the formulas as the principal active ingredient of compositions for treatment of malaria, the said compound can be included with other antimalarials to obtain advantageous combinations of properties. Such combinations include a compound of the formulas with quinine; with dimethyldiphenylsulfone; the 4-aminoquinolines, for example: amodiaquine, amopyroquine, cycloquine, chloroquine, hydroxychloroquine, oxychloroquine, and sontoquine; the 9- aminoaeridines, for example: quinacrine, azacrine, and aminoacrichine; the 8-aminoquinolines, for example: pamaquine, fourneau 710, certuna, pentaquine, isopentaquine, primaquine, and quinocide; the biguanides, for example: proguanil, chloroproguanil, and chloroazine; the diaminopyrimidines, for example: pyrimethamine; the long-acting sulfonamides, for example: sulfadiazine, sulphormethoxine, sulfadimethoxine, and sulfamethoxypyridazino.

The dosage of the formulas for treatment depends on route and frequency of administration; the age, weight, and condition of the patient; and the particular malaria parasite to be treated. A daily dosage schedule of from about 0.5 to 200 mg/kg parenterally and from 1 to 300 mg/kg orally embraces the effective range for treatment. The preferred dosage range is from 5 to 50 mg/kg parenterally and 25 to 100 mg/kg orally. The oral suppressive dose can be as low as one-tenth the above treatment dose.

A compound of the formulas is compounded with a suitable pharmaceutical carrier in unit dosage form for convenient and effective administration. In the preferred embodiments of this invention, the dosage units contain 10, 25, 50, 100, 250, and 500 mg amounts of a compound of the formulas for systemic treatment; 5 to 65 percent w/v for parenteral treatment. The dosage of compositions containing a compound of the formulas and one or more other active ingredients is to be determined with reference to the usual dosage of each such ingredient.

The novel compounds of this invention when administered orally are effective, as disclosed above, in the treatment and prevention of coccidiosis in poultry. These compounds are most conveniently fed to poultry as a component of the feed or drinking water of the animals although they may also be administered orally dispersed or admixed with other carriers or diluents. According to one aspect of the invention, novel compositions are provided in which a novel compound of this invention is present as an anticoccidial ingredient. Such compositions comprise a novel compound of this invention intimately dispersed in or admixed with an inert carrier or diluent. By inert carrier is meant one that is substantially nonreactive with respect to the compound of this invention physically coupled therewith and that may be administered orally with safety to the animals. The preferred compositions of this type, that is, where the compound of this invention is present as an anticoccidial ingredient, are those in which the anticoccidially active ingredient is intimately dispersed or suspended in or admixed with the normal elements of poultry sustenance. By normal elements of poultry sustenance is meant the feed and drink normally partaken by the poultry such as grain, water and/or other liquids. However, as indicated above, compositions comprising a compound of this invention intimately dispersed in or admixed with any carrier or diluent which is substantially inert with respect thereto, orally ingestable and tolerated by the animals, may be satisfactorily employed.

The amount of novel compound of this invention required for the control of coccidiosis in the poultry will, of course, vary somewhat, depending upon the specific compound or combination of two or more compounds of this invention employed. In general, the compounds of this invention are effective in the prevention of that disease without undesirable side effects when administered at levels at less than 0.05% by weight of the feed. Thus, concentrations of about 0.02% to 0.05% by weight of the feed may be advantageously administered in treating an established outbreak of coccidiosis. When these novel compounds are employed as therapeutic agents it is desirable to employ the lowest levels that afford fully adequate control of coccidiosis in order to eliminate as far as possible any risk of side effects that might appear on prolonged feeding of the compound.

In the preparation of solid compositions a uniform dispersion or admixture of the chosen compound of this invention throughout the carrier can be readily effected by the usual methods of grinding, stirring, milling or tumbling. By altering the amount of drug added, and the carrier used, compositions of varying concentrations may be made to suit any purpose.

According to another aspect of the invention, novel compositions are provided in which the novel anticoccidially active ingredient is present in relatively large amounts which are suitable for addition to the poultry feed either directly or after an intermediate dilution or blending step. These compositions which are commonly referred to in the art as feed supplements and are a preferred feature of this invention provide a more convenient way of obtaining a uniform distribution in the feed of relatively small amounts of the active ingredient required for an effective dosage. Any orally ingestable solid carrier which is substantially inert with respect to the novel compound of this invention employed and tolerated by the animals may be satisfactorily employed. Examples of carriers or diluents suitable for such compositions are solid orally ingestable carriers such as distillers' dried grains, corn meal, citrum meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone and the like. The novel compounds of this invention are intimately dispersed or admixed throughout the solid inert carrier by methods such as grinding, stirring, milling or tumbling. By selecting proper diluents and by altering the ratio of carrier to active ingredient, compositions of any desired concentration may be prepared. Formulations containing from about 1% to about 40% by weight, and preferably from about 2–25% by weight, of active ingredient are particularly suitable for addition to poultry feed. The active novel compound is normally dispersed or mixed uniformly in the diluent but in some instances may be sorbed on the carrier. The optimal concentration of coccidiostat in these feed supplements will depend to some extent on the particular compound employed. Since it is convenient for the feed manufacturer to use about one pound of feed supplement for each ton of finished feed, the preferred concentration of any one of our coccidiostats in a feed supplement is partly a function of the level of active ingredient desired in the finished feed.

The parent compounds disclosed in Chart 2 can be prepared by the procedures disclosed in pending U.S. patent application Ser. No. 148,056.

The 3-(5'-ribonucleotides) of the compounds of Chart 2 can be prepared by following the procedures disclosed in U.S. Pat. No. 3,671,647. Salts of these nucleotides also can be prepared following the procedures in U.S. Pat. No. 3,671,647.

Formulations of the nucleotides of this invention can be made following the composition examples in U.S. patent application Serial No. 148,056. The formulations are prepared by substituting a nucleotide of the subject invention for the active compound in the examples. The substitution can be on an equimolar basis.

General assay and characterization procedures which can be employed to determine and characterize the nucleotides of the invention are as follows:

Assay of 3-(5'-Ribonucleotides)

Since the 3-ribonucleotides of this invention lack in vitro antibacterial activity, their formation from the antibacterially-active parent compounds can be followed easily by measuring the loss of such antibiotic activity. To determine the amounts of antibacterially-active parent compound in culture filtrates or reaction mixtures, a standard assay with *Sarcina lutea* ATCC 9341 (is employed. To assay for the presence of the 3-ribonucleotides in fermentation beers, extracts, and purified materials, the phsophodiester bond is first hydrolyzed with crude alkaline phosphatase, or snake venom phosphodiesterase, by the procedures described below. The antibacterially-active compound in the hydrolysate is determined by standard assay.

Enzymatic Hydrolyses

Alkaline Phosphatase: Stock solutions (0.5 mg/ml, 0.54 Units/mg) of pigeon intestine alkaline phosphatase, EC 3.1.3.1 (Sigma) are prepared in Tris (hydroxymethyl) aminomethane hydrochloride buffer, 0.01 M pH 8.0. Samples to be treated are diluted 1:2 with the enzyme buffer mixture and are incubated at 28° C. for 18 hours.

Snake Venom Phosphodiesterase: Stock solutions (100 mg/ml, 0.026 Units/mg) of purified snake venom phosphodiesterase EC 3.1.4.1 (Sigma) are prepared in distilled water. Incubation mixtures contain 0.2 ml of a solution (1 mg/ml) of the sample to be treated in water, 0.6 ml of 0.01 M Tris-hydrochloride buffer, pH 9.0, 0.1 ml of 0.3 M $MgCl_2$, and 0.1 ml of the enzyme stock solution. Incubation is carried out at 37° C. for 18 hours.

Spleen Phosphodiesterase: Stock solutions of spleen phosphodiesterase EC 3.1.4.18 (Sigma) are prepared (1 mg/ml, 19.6 Units/mg) in distilled water. Incubation mixtures contain 0.4 ml of a solution (0.5 mg/ml) of the sample to be treated in water, 0.5 ml of 0.02 M Tris buffer, pH 7.0 and 0.1 ml of the enzyme stock solution. Incubation is carried out at 37° C. for 18 hours.

Thin-Layer Chromatographic Analysis of Preparation and Enzymatic Hydrolysates.

The production and purification of the 3-ribonucleotides is followed by assay against *S. lutea* (see above) and ty TLC using silica gel G and methyl ethyl ketone-acetone-water (186:52:20, v/v) or ethyl acetate-acetone-water (8:5:1) as the solvent systems. The bioactive parent compounds are detected by bioautography on agar seeded with *S. lutea*.

The products of enzymatic or chemical hydrolysis of the 3-nucleotides are separated by the following TLC systems:

A: Silica gel GF plates (Analtech Inc.); water as the solvent system.
B. Silica gel GF plates; n-propyl alcohol-conc. ammonium hydroxide-water (55:10:35, v/v).
C. NM-Polygram Cellulose 300 (Brinkman Instruments Inc.); 1-butanol-water-formic acid (77:13:10, v/v).

UV absorbing materials are detected by a short wafelength UV lamp. Bioinactive, UV-nonabsorbing materials are detected by a permanganate-periodate spray reagent. Bioactive nucleotide materials are detected by bioautography on agar seeded with *S. lutea*.

The following example shows the fermentation and purification procedures for preparing the nucleotide of the compound designated as U-57930E. The structural formula of U-57930E is shown in Chart 3. By following the procedures of this example, or obvious equivalents thereof, there can be made the 3-ribonucleotides of the other compounds disclosed in Chart 2.

Preparation of U-57930E Nucleotides

A. Fermentation Procedure

*Streptomyces rochei*, NRRL 3533, is grown in a medium consisting of glucose, 10 g/liter; Difco peptone, 4g/liter; Difco yeast extract, 4 g/liter; $MgSO_4.7H_2O$, 0.5 g/liter; $KH_2PO_4$, 2.0 g/liter; $K_2HPO_4$, 4 g/liter for three days at 28° C. on a rotary shaker. The mycelium from this growth is used to inoculate a fermentation medium containing the same ingredients. The fermentation is carried out for 48 hours at 28° C. on a rotary shaker. At the end of this 48-hour incubation, U-57930 is added to a final concentration of 50 mg/liter and the fermentation continued at 32° C. After twelve hours, additional U-57930 is added to make the total concentration 150 mg/liter. After twelve additional hours, the U-57930 concentration is increased to 250 mg/liter. The fermentation is continued at 32° for 24 hours after the last addition of U-57930. At this time the culture filtrates are harvested and found to contain no more than 1 mg/liter of U-57930. The remaining 249 mg/liter is converted to bioinactive material.

S. rochei, NRRL 3533, is a known microbe which is available to the public upon request from the NRRL repository. The address of this repository is as follows: Northern Utilization and Research Division, Agricultural Research Service, U.S. Department of Agriculture, Peoria, Ill., U.S.A.

B. Isolation and Purification Procedures

Isolation of U-57930 3-Ribonucleotides from Fermentation Broth

Adsorption on Amberlite XAD-2: Fermentation broth (ca 12 liter) containing 3 g of "inactivated" U-57930 is filtered at harvest pH (7.7) by using filter aid. The mycelial cake is washed with 1.2 liter of water and discarded. The clear filtrate and wash are combined and adjusted to pH 6.0 and passed over a column prepared from 600 ml of Amberlite XAD-2 (Rohm and Haas Co., Philadelphia, PA), at a flow rate of 40 ml/minute. The spent is tested for bioactivity before and after treatment with alkaline phosphatase and is discarded. The column is washed with 2 liters of water. The aqueous wash is also found bioinactive before and after treatment with alkaline phosphatase and is discarded. The column is then eluted with methanol-water (70:30 v/v). Fractions of 20 ml are collected at a rate of 20 ml/minute. Testing for bioactivity before (−E) and after (+E) treatment with alkaline phosphatase shows the following.

| Fraction No. | Zone (S. lutea) | |
|---|---|---|
| | −E | +E |
| 5 | 0 | 0 |
| 10 | 0 | 0 |
| 11 | 0 | 0 |
| 13 | 0 | 36 |
| 20 | 33 | 55 |
| 25 | 32 | 54 |
| 40 | 31 | 50 |
| 45 | 29 | 48 |
| 50 | 26 | 39 |
| 55 | 23 | 38 |
| 60 | 21 | 37 |
| 65 | 19 | 27 |
| 70 | 17 | 26 |
| 75 | 17 | 26 |
| 80 | 16 | 26 |
| 85 | 16 | 26 |
| 90 | 16 | 26 |
| 95 | 16 | 26 |
| 100 | 16 | 26 |
| 110 | 16 | 21 |
| 120 | 15 | 21 |
| 130 | 15 | 21 |
| 140 | 15 | 21 |
| 150 | 15 | 21 |
| 160 | 15 | 21 |

-continued

| Fraction No. | Zone (S. lutea) | |
|---|---|---|
| | −E | +E |
| 170 | 15 | 21 |
| 180 | 15 | 21 |
| 190 | 15 | 21 |
| 200 | 15 | 21 |

Fractions 12–80 are combined, concentrated to an aqueous solution and freeze-dried to give prep ADA-34.1, 12.22 g.

In another series of experiments, 6 liters of fermentation broth containing 2 g of "inactivated" U-57930 is treated as described above. The methanolic eluates from the Amberlite XAD-2 column are kept as ADA-143B. This solution is not concentrated to dryness; instead, it is purified by Dowex-1 Chromatography as described below.

Dowex-1 Chromatography: The column is prepared from 300 ml of Dowex-1 (X-4) in the acetate form. The methanolic solution, ADA-143B pH 8.2 is passed through the column. The spent is collected at a rate of 2.5 ml/minute in 20 ml-fractions. (Fractions 1–60). The column is washed with 1.5 liter of water (10 ml/min; fractions 66–108). The column is then eluted with 5% acetic acid (rate, 10 ml/minute; fractions 109–310). The following pools are made:

| Pool | Fractions | Volume | Label |
|---|---|---|---|
| 1 | Fractions 1–80 | 1000 ml | (ADA-1A) |
| 2 | Fractions 81–110 | 600 ml | (ADA-2A) |
| 3 | Fractions 111–130 | 450 ml | (ADA-3A) |
| 4 | Fractions 131–150 | 450 ml | (ADA-4A) |
| 5 | Fractions 151–190 | 900 ml | (ADA-5A) |
| 6 | Fractions 191–230 | 900 ml | (ADA-6A) |
| 7 | Fractions 231–270 | 900 ml | (ADA-7A) |
| 8 | Fractions 271–310 | 900 ml | (ADA-8A) |

Testing before (−E) and after (+E) treatment with alkaline phosphatase shows the following:

| | Zone (S. lutea) | |
|---|---|---|
| | −E | +E |
| Pool 1 | 31 | 52 |
| 2 | 36 | 49 |
| 3 | 34 | 45 |
| 4 | 18 | 40 |
| 5 | 25 | 30 |
| 6 | 27 | 29 |
| 7 | 27 | 29 |
| 8 | 29 | 31 |

Pools 1 and 2 are combined, concentrated to an aqueous solution and freeze-dried to give prep ADA-2.1, 1.48 g.

Pools 3 and 4 are also combined and treated similarly to give ADA-2.2, 2.5 g.

Preparations ADA−2.1 and −2.2 give U-57930 after treatment with alkaline phosphatase.

Preparations ADA−34.1, −2.1 and −2.2 are combined and purified by the counter double current distribution procedure described below.

Counter Double Current Distribution: The material obtained by combination of preparations ADA−34.1, −2.1 and −2.2, 16.20 g, is dissolved in 25 ml of each phase of the solvent system consisting of equal volumes of 1-butanol-water (1:1). The solutions are added in the center tubes of an all-glass counter double current distribution apparatus (100 tubes, 25 ml/phase). The distribution is analyzed, after 150 transfers, for bioactivity before (−E) and after (+E) treatment with alkaline phosphatase. Results follow:

|  | Zone (*S. lutea*-sensitive) | |
| --- | --- | --- |
|  | −E | +E |
| Lower Collector | | |
| 5 | 29 | 31 |
| 10 | 31 | 33 |
| 15 | 30 | 33 |
| 20 | 27 | 33 |
| 25 | 22 | 33 |
| 30 | 17 | 34 |
| 35 | 0 | 34 |
| 40 | 0 | 33.5 |
| 45 | 0 | 33 |
| 50 | 0 | 34 |
| 55 | 0 | 34 |
| 60 | 0 | 35 |
| 65 | 0 | 36 |
| 70 | 0 | 38 |
| 75 | 0 | 39 |
| 80 | 0 | 40 |
| 85 | 0 | 41 |
| 90 | 0 | 42 |
| 95 | 0 | 43 |
| 100 | 0 | 43.5 |
| Lower Machine | | |
| 50 | 0 | 45 |
| 45 | trace | 46 |
| 40 | 15 | 47 |
| 35 | 17 | 47.5 |
| 30 | 17 | 47 |
| 25 | 18 | 47 |
| 20 | 17.5 | 48 |
| 15 | 17 | 48 |
| 10 | 16 | 48 |
| 5 | 15 | 50 |
| 0 | trace | 50 |
| Upper Machine | | |
| 5 | trace | 49 |
| 10 | trace | 48.5 |
| 15 | trace | 48 |
| 20 | trace | 48.5 |
| 25 | trace | 49 |
| 30 | 30 | 50 |
| 35 | trace | 51 |
| 40 | 15 | 52 |
| 45 | 16 | 53 |
| 50 | 21 | 54 |
| Upper Collector | | |
| 100 | 17.5 | 54 |
| 95 | 17 | 53.5 |
| 90 | 19 | 53.5 |
| 85 | 20 | 53.5 |
| 80 | 21 | 53.5 |
| 75 | 22 | 53.5 |
| 70 | 24 | 53.5 |
| 65 | 26 | 53.5 |
| 60 | 28 | 53.5 |
| 55 | 30 | 52.5 |
| 50 | 32.5 | 52 |
| 45 | 33 | 52 |
| 40 | 35 | 52 |
| 35 | 36 | 52 |
| 30 | 39 | 49 |
| 25 | 41 | 47 |
| 20 | 43 | 48 |
| 15 | 43 | 46 |
| 10 | 43 | 43 |
| 5 | 35 | 35 |

The following pools are made. Each pool is concentrated to an aqueous solution and freeze-dried to give the corresponding preparations.
Pool I: Lower collector 1–50;
Pool II: Lower collector 51–100; lower machine 50–30;
Pool III: Lower machine 29–0; Upper machine 1–50; Upper collector 100–30.
Preparations obtained are:
From pool I, prep. ADA−47.1, 9.78 g
From pool II, prep. ADA−47.2, 0.30 g
From pool III, prep. ADA−47.3, 5.29 g Preparations ADA−47.2 and −47.3 are combined and purified by DEAE-Sephadex chromatography as described below.

DEAE-Sephadex Chromatography: Three hundred g of DEAE-Sephadex (A-25) are stirred for 1 hour with water and for 2 hours with 0.5 N aqueous sodium hydroxide. The ionic exchanger is washed with water until the pH is ca 7.5. The material is then stirred for 2 hours with 0.5 N aqueous acetic acid, washed with water to a neutral pH, and poured into a column and packed under 2 lbs pressure to a constant height. The column is washed with 4 liters of water, 8 liters of 0.1% aqueous solution of tris-(hydroxymethyl)aminomethane (THAM), and 3 liters of 0.03 M THAM acetate buffer pH 8.0 (prepared by dissolving 3.64 g of THAM in 800 ml water, adjusting the pH to 8.0 with glacial acetic acid and then adjusting the volume to 1 liter).

Starting material, preparations ADA−47.2 and 47.3 ca 5.50 g, is dissolved in 20 ml of 0.03 M THAM acetate pH 8.0 buffer and added on the top of the column. The column is then eluted downflow with 0.3 M THAM acetate pH 8.0 buffer. Fractions 1–190 (20 ml) are collected. At this point elution of the column is continued in an upflow manner. Fractions A, B, C, D, and E (1 liter each) are collected. Testing for bioactivity before (−E) and after (+E) treatment with alkaline phosphatase shows the following:

| Fraction No. | Zone (*S. lutea*-sensitive) | |
| --- | --- | --- |
|  | −E | +E |
| 3 | 0 | 0 |
| 6 | 0 | 0 |
| 9 | 0 | 0 |
| 12 | 0 | 0 |
| 15 | 0 | 0 |
| 18 | 0 | 0 |
| 21 | 0 | 0 |
| 24 | 0 | 0 |
| 27 | 0 | 0 |
| 30 | 0 | 0 |
| 33 | 0 | 0 |
| 36 | 38 | 39 |
| 39 | 43.5 | 44 |
| 42 | 36 | 36 |
| 45 | 23.5 | 23 |
| 48 | 15 | 16 |
| 51 | 0 | 0 |
| 54 | 0 | 0 |
| 57 | 0 | 0 |
| 60 | 0 | 0 |
| 63 | 0 | 0 |
| 66 | 0 | 0 |
| 69 | 15 | 16 |
| 72 | 17 | 20 |
| 75 | 21 | 26 |
| 78 | 23 | 27 |
| 81 | 23 | 30 |
| 84 | 23 | 29 |
| 87 | 22 | 24 |
| 90 | 21 | 23 |
| 93 | 21 | 24 |
| 96 | 22 | 26 |
| 99 | 21 | 35 |
| 102 | 22 | 44 |
| 105 | 23 | 51 |
| 108 | 22.5 | 54 |
| 111 | 22.5 | 52.5 |

-continued

| Fraction No. | Zone (*S. lutea*-sensitive) | |
|---|---|---|
| | −E | +E |
| 114 | 22 | 52 |
| 117 | 22 | 54.5 |
| 120 | 20.5 | 56 |
| 123 | 20 | 56 |

The following pools are made:

| | |
|---|---|
| Pool I | Fractions 34–38, 280 ml (ADA-69B) |
| Pool II | Fractions 75–90, 330 ml (ADA-69C) |
| Pool III | Fractions 101–111, 180 ml (ADA-69D) |
| Pool IV | Fractions 114–150, 580 ml (ADA-69E) |
| Pool V | Fractions 151–164, 100 ml (ADA-69F) |
| Pool VI | Fractions 165–186, 125 ml (ADA-69G) |
| Pool VII | Fraction C, 1 liter (ADA-69A) |

Pool I (ADA−69B) contains unchanged U-57930 and is discarded.

Pool II (ADA−69C) contains an unknown material which yields U-57930 by treatment with alkaline phosphatase. UV: λmax 275 nm.

Pool III (ADA−69D) contains U-57930 cytidylate and is treated as described later. UV: λmax 270 nm.

Pool IV (ADA−69E) contains U-57930 adenylate and is treated as described later. UV: λmax 260 nm.

Pool V (ADA−69F) contains a mixture of U-57930 adenylate, U-57930 uridylate and U-57930 guanylate. This solution is treated as described later.

Pool VI (ADA−69G) contains U-57930 guanylate and is treated as described later. UV: λmax 254; sh at 275.

Pool VII (ADA−69A) contains a mixture of U-57930 guanylate and U-57930 uridylate. This solution is treated as described later.

Isolation of Essentially Pure U-57930-Cytidylate, U-57930-Adenylate and U-57930-Guanylate from Pools III, IV and VI, Respectively. Removal of THAM Acetate Buffer by Amberlite XAD-2 Chromatography: Pools III, IV and VI, obtained as described above, are passed over columns containing Amberlite XAD-2. The spents are discarded. The columns are washed with water and then eluted with methanol-water (70:30 v/v). Fractions are analyzed by UV and by testing for bioactivity before and after treatment with alkaline phosphatase. Appropriate fractions are combined, concentrated to an aqueous solution and freeze-dried. Details on the amount of Amberlite XAD-2 used for each pool, the amount of water wash, the amount of methanolic eluate and the amount of material obtained are listed in the following table.

| Pool | Amberlite XAD-2 Used (ml) | Water Wash (ml) | Methanolic Eluate (ml) | Isolated Material (mg) |
|---|---|---|---|---|
| III | 50 | 200 | 300 | 150 |
| IV | 200 | 800 | 600 | 3510 |
| VI | 50 | 200 | 300 | 470 |

The material obtained from pool III is kept as ADA−73.1; from pool IV as ADA−74.1; and from pool VI as ADA−75.1.

Removal of THAM Acetate Buffer from Pool V (ADA−69F) and Pool VII (ADA−69A) by Amberlite XAD-2 Chromatography: The column is prepared from 300 ml of Amberlite XAD-2. Pools V and VII containing a mixture of U-57930 adenylate; U-57930-uridylate and U-57930 guanylate are passed through the column. The spent is discarded. The column is washed with 600 ml of water. The spent is discarded. The column is eluted with methanol-water (70:30). Fractions yielding bioactive material after treatment with alkaline phosphatase are combined, 300 ml, concentrated to an aqueous solution and freeze-dried to give prep ADA−71.1, 670 mg. Prep −71.1 is treated as described below.

Separation of U-57930 Uridylate from U-57930-Adenylate and U-57930-Guanylate. DEAE-Sephadex Chromatography. Six hundred ml of DEAE-Sephadex in the acetate form, prepared as described earlier, are washed with 0.03 M THAM acetate pH 8.0 buffer and packed into a glass column (ID, 4.5 cm; height, 40 cm) under hydrostatic pressure.

Prep ADA−71.1 (see above) is dissolved in 10 ml of 0.03 M THAM acetate pH 8.0 buffer and added on the top of the column. The column is eluted with:
(1) 0.03 M THAM acetate, pH 8.0 (Fractions 1–79)
(2) 0.12 M THAM acetate, pH 8.0 (Fractions 80–395)
(3) 0.25 M THAM acetate, pH 8.0 (Fractions 396–750)

Fractions of 20 ml are collected and analyzed by UV and by testing for bioactivity before and after treatment with alkaline phosphatase. Fractions 51–60 contain U-57930 adenylate; fractions 62–73 (ADA−94.B) contain U-57930 uridylate; fractions 74–110 contain U-57930 guanylate).

Isolation of Essentially Pure U-57930 Uridylate. Removal of THAM-Acetate Buffer by Amberlite XAD-2 Chromatography. The column is prepared from 50 ml of Amberlite XAD-2. Pool ADA−94B, containing U-57930 uridylate, is passed over the column at a rate of 2 ml/minute. The spent is discarded. The column is washed with 200 ml of water. The wash is discarded. The column is eluted with methanol-water (70:30 v/v). Fractions containing (by UV) U-57930 uridylate are combined (200 ml), concentrated to an aqueous solution, and freeze-dried to give ADA−95.1, 60 mg.

CHARACTERIZATION OF U-57930 3'(5'-CYTIDYLATE)

1. IR Tabulation

Tables listing the IR absorptions (Nujol and KBr) are as follows:

| Band Freq. | Inten. | Type | Band Freq. | Inten. | Type |
|---|---|---|---|---|---|
| 3417.3 | 24 | SH | 1249.0 | 33 | SH |
| 3341.1 | 19 | BRD | 1214.3 | 21 | AVG |
| 3211.8 | 19 | BRD | 1146.8 | 42 | SH |
| 3108.6 | 25 | BRD | 1089.9 | 15 | BRD |
| 2951.4 | 2 | BRD M | 1070.6 | 12 | AVG |
| 2926.3 | 1 | BRD M | 1056.1 | 14 | SH |
| 2854.9 | 2 | BRD M | 992.4 | 39 | AVG |
| 2729.6 | 48 | BRD M | 972.2 | 39 | AVG |
| 2693.9 | 51 | SH | 955.8 | 49 | SH |
| 2535.7 | 65 | SH | 930.7 | 51 | AVG |
| 1649.3 | 8 | AVG | 889.2 | 36 | AVG |
| 1610.7 | 26 | AVG | 860.3 | 52 | AVG |
| 1575.0 | 35 | AVG | 849.7 | 53 | AVG |
| 1528.7 | 31 | AVG | 804.4 | 46 | SH |
| 1489.2 | 23 | AVG | 788.9 | 40 | AVG |
| 1462.2 | 9 | AVG M | 721.4 | 44 | AVG M |
| 1404.3 | 41 | BRD | 705.0 | 47 | BRD |
| 1377.3 | 18 | AVG M | 654.9 | 45 | SH |
| 1368.6 | 31 | SH M | 632.7 | 38 | AVG |
| 1286.6 | 34 | AVG | | | |

Band Freq.: Band Frequencies in Wavenumbers (cm−1)
Inten.: Intensity in percent transmittance (%T)
Data Type in Local Peak Region: BRD—Broad; AVG—Average; SHP—Sharp; SH—Shoulder
Peak list edited. *Indicates peaks added.
M: Possible interference from mineral oil.

| 25 Strongest Peaks | | | |
|---|---|---|---|
| % T | Freq. | % T | Freq. |
| 1 | 2926.2 | 24 | 3417.2 |
| 2 | 2951.3 | 25 | 3108.5 |
| 2 | 2854.8 | 26 | 1610.6 |
| 8 | 1649.2 | 31 | 1528.6 |
| 9 | 1462.1 | 31 | 1368.5 |
| 12 | 1070.5 | 33 | 1249.0 |
| 14 | 1056.0 | 34 | 1286.5 |
| 15 | 1089.8 | 35 | 1575.0 |
| 18 | 1377.2 | 36 | 889.1 |
| 19 | 3341.0 | 38 | 632.6 |
| 19 | 3211.7 | 39 | 992.3 |
| 21 | 1214.2 | 39 | 972.1 |
| 23 | 1489.1 | | |

Prep: Mineral Oil Mull
Max %T: 87 @ 1848.0
%T at 3800 (cm−1): 83
Density (cm−1/pt): 0.964

| Band Freq. | Inten. | Type | Band Freq. | Inten. | Type |
|---|---|---|---|---|---|
| 3408.6 | 10 | BRD | 1088.9 | 12 | BRD |
| 3102.8 | 26 | SH | 1071.5 | 9 | AVG |
| 2963.9 | 28 | AVG | 1057.1 | 11 | SH |
| 2930.2 | 27 | BRD | 992.4 | 35 | AVG |
| 2878.1 | 37 | AVG | 972.2 | 36 | AVG |
| 2862.7 | 39 | SH | 956.8 | 45 | SH |
| 2768.1 | 51 | SH | 928.8 | 48 | AVG |
| 2511.6 | 65 | BRD | 889.2 | 32 | AVG |
| 1649.3 | 4 | AVG | 859.3 | 47 | AVG |
| 1614.6 | 20 | SH | 851.6 | 47 | SH |
| 1576.0 | 30 | AVG | 804.4 | 39 | SH |
| 1528.7 | 28 | AVG | 788.9 | 34 | AVG |
| 1491.1 | 21 | AVG | 743.6 | 47 | SH |
| 1462.2 | 33 | AVG | 705.0 | 40 | AVG |
| 1450.6 | 35 | SH | 654.9 | 39 | SH |
| 1404.3 | 37 | AVG | 634.6 | 35 | AVG |
| 1384.0 | 33 | AVG | 595.1 | 33 | AVG |
| 1360.9 | 42 | SH | 572.9 | 33 | AVG |
| 1286.6 | 32 | AVG | 525.6 | 32 | AVG |
| 1251.9 | 30 | SH | 447.5 | 36 | AVG |
| 1215.2 | 18 | AVG | | | |

Band Freq.: Band Frequencies in wavenumbers (cm−1)
Inten.: Intensity in Percent Transmittance (%T)
Data Type in Local Peak Region: BRD—Braod; AVG—Average; SHP—Sharp; SH—Shoulder
Peak List Edited. *Indicates peaks added.

| 25 Strongest Peaks | | | |
|---|---|---|---|
| % T | Freq. | % T | Freq. |
| 4 | 1649.2 | 30 | 1251.8 |
| 9 | 1071.5 | 32 | 1286.5 |
| 10 | 3408.5 | 32 | 889.1 |
| 11 | 1057.0 | 32 | 525.5 |
| 12 | 1088.8 | 33 | 1462.1 |
| 18 | 1215.1 | 33 | 1384.0 |
| 20 | 1614.5 | 33 | 595.0 |
| 21 | 1491.0 | 33 | 572.8 |
| 26 | 3102.7 | 34 | 788.8 |
| 27 | 2930.1 | 35 | 1450.5 |
| 28 | 2963.8 | 35 | 992.3 |

| 25 Strongest Peaks | | | |
|---|---|---|---|
| % T | Freq. | % T | Freq. |
| 28 | 1528.6 | 35 | 634.5 |
| 30 | 1576.0 | | |

Prep: KBR Pellet
Max %T: 100 @ 403.1
%T at 4000 (cm−1): 78
Density (cm−1/pt): 0.964

2. UV Absorption Spectrum [λmax (a)]

In water at:
pH 2.0, 279 nm (6.5)
pH 7.0, 270 nm (9.9)
pH 11.0, 271 (9.6)

3. Elemental Composition

Mol. formula: $C_{26}H_{43}N_5O_{12}$ SClP. Molecular Weight, 715. Calcd: C, 43.64; H, 6.01; N, 9.79; O, 26.88; S, 4.47; Cl, 4.89; P, 4.33.

4. Optical Rotation $[\alpha]_D^{25}$, +107° (C, 0.854, water)

5. Solubilities

Highly soluble in water, methanol and ethanol. Slightly soluble in acetone and other ketones, ethyl acetate and other esters, chloroform, methylene chloride. Insoluble in saturated hydrocarbon solvents.

6. Antibacterial Activity

U-57930 3-(5′-cytidylate) is not active in vitro. However, treatment with alkaline phosphatase or phosphodiesterase I yields U-57930 which is highly active against a variety of G+ organisms, both in vitro and in vivo.

7. Melting point: 205°–207° (with decomposition).

CHARACTERIZATION OF U-57930 3′(5′-ADENYLATE)

1. IR Tabulation

Tables listing the IR absorptions (Nujol and KBr) are as follows:

| Band Freq. | Inten. | Type | Band Freq. | Inten. | Type |
|---|---|---|---|---|---|
| 3335.3 | 16 | BRD | 1245.1 | 24 | SH |
| 3267.8 | 17 | BRD | 1213.3 | 17 | AVG |
| 3210.8 | 17 | BRD | 1175.7 | 43 | SH |
| 2954.3 | 3 | BRD M | 1146.8 | 40 | SH |
| 2924.4 | 2 | BRD M | 1089.9 | 13 | AVG |
| 2868.4 | 6 | SH M | 1069.6 | 10 | AVG |
| 2854.9 | 4 | AVG M | 1055.1 | 13 | SH |
| 2727.6 | 46 | BRD M | 991.5 | 35 | AVG |
| 2520.2 | 61 | BRD | 972.2 | 36 | AVG |
| 1684.0 | 22 | SH | 957.7 | 45 | SH |
| 1641.6 | 14 | AVG | 930.7 | 48 | AVG |
| 1600.1 | 28 | AVG | 889.2 | 32 | AVG |
| 1576.0 | 31 | AVG | 861.3 | 47 | AVG |
| 1550.9 | 43 | SH | 848.7 | 49 | AVG |
| 1509.4 | 53 | SH | 818.8 | 45 | AVG |
| 1463.1 | 15 | AVG M | 798.6 | 40 | AVG |
| 1420.7 | 35 | AVG | 722.4 | 36 | AVG M |
| 1377.3 | 24 | AVG M | 708.9 | 40 | SH |
| 1367.6 | 35 | SH M | 647.1 | 33 | SH |
| 1332.0 | 36 | AVG | 635.6 | 31 | AVG |
| 1299.2 | 34 | AVG | | | |

Band Freq.: Band Frequencies in Wavenumbers (cm−1)
Inten.: Intensity in percent transmittance (%T)
Data Type in Local Peak Region: BRD—Broad; AVG—Average; SHP—Sharp; SH—Shoulder
Peak list edited. *Indicates peaks added.
M: Possible interference from mineral oil.

| 25 Strongest Peaks | | | |
|---|---|---|---|
| % T | Freq. | % T | Freq. |
| 2 | 2924.3 | 22 | 1684.0 |
| 3 | 2954.2 | 24 | 1377.2 |
| 4 | 2854.8 | 24 | 1245.0 |
| 6 | 2868.3 | 28 | 1600.0 |
| 10 | 1069.5 | 31 | 1576.0 |
| 13 | 1089.8 | 31 | 635.5 |
| 13 | 1055.0 | 32 | 889.1 |
| 14 | 1641.5 | 33 | 647.0 |
| 15 | 1463.0 | 34 | 1299.1 |
| 16 | 3335.2 | 35 | 1420.6 |
| 17 | 3267.7 | 35 | 1367.5 |
| 17 | 3210.7 | 35 | 991.5 |
| 17 | 1213.2 | | |

Prep: Mineral Oil Mull
Max %T: 85 @ 1864.4
%T at 3800 (cm−1): 81
Density (cm−1/pt): 0.964

| Band Freq. | Inten. | Type | Band Freq. | Inten. | Type |
|---|---|---|---|---|---|
| 3375.8 | 7 | BRD | 1090.8 | 8 | AVG |
| 3223.4 | 10 | BRD | 1069.6 | 5 | AVG |
| 3124.0 | 17 | SH | 1050.3 | 8 | SH |
| 2963.0 | 22 | AVG | 990.5 | 27 | AVG |
| 2929.2 | 22 | BRD | 972.2 | 29 | AVG |
| 2878.1 | 31 | AVG | 956.8 | 38 | SH |
| 2863.6 | 33 | SH | 929.8 | 42 | AVG |
| 2756.6 | 45 | BRD | 889.2 | 24 | AVG |
| 2521.2 | 60 | BRD | 861.3 | 38 | AVG |
| 2188.5 | 75 | BRD | 851.6 | 40 | SH |
| 1678.2 | 15 | SH | 818.8 | 36 | AVG |
| 1643.5 | 7 | AVG | 807.3 | 36 | BRD |
| 1602.0 | 20 | AVG | 798.6 | 30 | AVG |
| 1576.0 | 23 | AVG | 768.7 | 41 | BRD |
| 1553.8 | 35 | SH | 721.4 | 30 | AVG |
| 1511.4 | 49 | SH | 706.9 | 31 | BRD |
| 1475.7 | 27 | AVG | 648.1 | 26 | AVG |
| 1421.7 | 29 | AVG | 636.5 | 26 | AVG |
| 1384.0 | 32 | AVG | 584.5 | 28 | SH |
| 1332.0 | 31 | AVG | 571.9 | 26 | AVG |
| 1301.1 | 28 | AVG | 533.3 | 27 | SH |
| 1246.1 | 19 | SH | 522.7 | 25 | AVG |
| 1215.2 | 12 | AVG | 503.4 | 25 | AVG |
| 1176.7 | 36 | SH | | | |

Band Freq.: Band Frequencies in Wavenumbers (cm−1)
Inten.: Intensity in percent transmittance (%T)
Data Type in Local Peak Region: BRD—Broad; AVG—Average; SHP—Sharp; SH—Shoulder
Peal list edited. *Indicates peaks added.

| 25 Strongest Peaks | | | |
|---|---|---|---|
| % T | Freq. | % T | Freq. |
| 5 | 1069.5 | 23 | 1576.0 |
| 7 | 3375.7 | 24 | 889.1 |
| 7 | 1643.5 | 25 | 522.6 |
| 8 | 1090.7 | 25 | 503.3 |
| 8 | 1050.2 | 26 | 648.0 |
| 10 | 3223.3 | 26 | 636.5 |
| 12 | 1215.1 | 26 | 571.8 |
| 15 | 1678.1 | 27 | 1475.6 |
| 17 | 3124.0 | 27 | 990.5 |
| 19 | 1246.0 | 27 | 533.2 |
| 20 | 1602.0 | 28 | 1301.0 |
| 22 | 2963.0 | 28 | 584.5 |
| 22 | 2929.1 | | |

Prep: KBR Pellet
Max %T: 95 @ 405.0
%T at 4000 (cm−1): 77
Density (cm−1/pt): 0.964

2. UV Absorption Spectrum [λmax (a)]

In water at:
pH 2.0, 258 (16.0)
pH 7.0, 261 (16.5)
pH 11.0, 261 (16.0 )

3. Elemental Composition

Molecular formula: $C_{27}H_{43}N_7O_{10}$ SCIP. Molecular Weight, 723. Calcd C, 44.81; H, 5.94; N, 13.55; O, 22.13; S, 4.42; Cl, 4.84; P, 4.28. Found N, 12.87; S, 5.39; Cl, 4.76; P, 3.83.

4. Optical Rotation $[\alpha]_D^{25}$, +94° (C, 0.887, water).

5. Solubilities

Highly soluble in water, methanol and ethanol. Slightly soluble in acetone and other ketones, ethyl acetate and other esters, chloroform and methylene chloride. Insoluble in saturated hydrocarbon solvents.

6. Antibacterial Activity

U-57930 [3-(5′-adenylate)] is not active in vitro. However, treatment with alkaline phosphatase or phosphodiester I yields U-57930, which is highly active against a variety of G+ organisms both in vitro and in vivo. U-57930 3-(5′-adenylate) was found active in vivo (subcutaneously, mice) with a $CD_{50}$ of 0.62 (0.48-0.79) mg/kg. against *S. pyogenes*.

7. Melting Point: 203.5°-205° (with decomposition)

CHARACTERIZATION OF U-57930
3-(5′-URIDYLATE)

1. IR Tabulation

Tables listing the IR absorptions (Nujol and KBr) are as follows:

| Band Freq. | Inten. | Type | Band Freq. | Inten. | Type |
|---|---|---|---|---|---|
| 3330.4 | 19 | BRD | 1332.9 | 44 | BRD |
| 3224.4 | 21 | BRD | 1296.3 | 40 | SH |
| 2952.4 | 1 | BRD M | 1251.9 | 28 | BRD |
| 2924.4 | 0 | BRD M | 1215.2 | 19 | AVG |
| 2867.5 | 4 | SH M | 1089.9 | 13 | AVG |
| 2854.0 | 3 | AVG M | 1071.5 | 9 | AVG |
| 2733.4 | 49 | SH M | 1056.1 | 13 | SH |
| 2695.8 | 53 | SH | 991.5 | 39 | AVG |
| 2532.8 | 67 | SH | 973.2 | 39 | AVG |
| 1757.3 | 73 | SH | 957.7 | 48 | SH |
| 1685.9 | 8 | AVG | 931.7 | 49 | AVG |
| 1647.4 | 21 | SH | 890.2 | 34 | AVG |
| 1602.0 | 41 | AVG | 858.4 | 50 | AVG |
| 1574.1 | 42 | AVG | 813.0 | 43 | AVG |
| 1555.7 | 43 | BRD | 798.6 | 47 | AVG |
| 1462.2 | 12 | AVG M | 767.7 | 50 | AVG |
| 1425.5 | 37 | SH | 721.4 | 42 | AVG M |
| 1378.3 | 22 | AVG M | 634.6 | 35 | AVG |

| Band Freq. | Inten. | Type | Band Freq. | Inten. | Type |
|---|---|---|---|---|---|
| 1367.6 | 37 | SH M | | | |

Band Freq.: Band Frequencies in Wavenumbers (cm−1)
Inten.: Intensity in percent transmittance (%T)
Data Type in Local Peak Region: BRD—Broad; AVG—Average; SHP—Sharp; SH—Shoulder
This peak list is unedited.
M: Possible interference from mineral oil.

| 25 Strongest Peaks | | | |
|---|---|---|---|
| %T | Freq. | %T | Freq. |
| 0 | 2924.3 | 22 | 1378.2 |
| 1 | 2952.3 | 28 | 1251.8 |
| 3 | 2854.0 | 34 | 890.1 |
| 4 | 2867.5 | 35 | 634.5 |
| 8 | 1685.8 | 37 | 1425.5 |
| 9 | 1071.5 | 37 | 1367.5 |
| 12 | 1462.1 | 39 | 991.5 |
| 13 | 1089.8 | 39 | 973.1 |
| 13 | 1056.0 | 40 | 1296.2 |
| 19 | 3330.3 | 41 | 1602.0 |
| 19 | 1215.1 | 42 | 1574.0 |
| 21 | 3224.3 | 42 | 721.3 |
| 21 | 1647.3 | | |

Prep: Mineral Oil Mull
Max %T: 86 @ 3764.5
%T at 3800 (cm−1): 85
Density (cm−1/pt): 0.964

| Band Freq. | Inten. | Type | Band Freq. | Inten. | Type |
|---|---|---|---|---|---|
| 3387.4 | 12 | BRD | 1055.1 | 10 | SH |
| 3114.4 | 25 | SH | 992.4 | 35 | AVG |
| 2962.0 | 26 | AVG | 973.2 | 36 | AVG |
| 2931.1 | 26 | BRD | 956.8 | 45 | SH |
| 2879.1 | 36 | AVG | 929.8 | 48 | AVG |
| 2863.6 | 38 | SH | 889.2 | 31 | AVG |
| 2833.7 | 43 | SH | 859.3 | 46 | AVG |
| 2509.6 | 64 | BRD | 813.0 | 40 | AVG |
| 1685.0 | 6 | BRD | 811.1 | 40 | SH |
| 1647.4 | 17 | SH | 798.6 | 43 | AVG |
| 1605.9 | 35 | SH | 782.2 | 48 | BRD |
| 1576.0 | 37 | AVG | 768.7 | 48 | AVG |
| 1556.7 | 39 | BRD | 707.9 | 43 | AVG |
| 1463.1 | 31 | AVG | 669.3 | 43 | SH |
| 1423.6 | 35 | AVG | 649.1 | 40 | SH |
| 1384.0 | 32 | AVG | 634.6 | 37 | AVG |
| 1331.0 | 43 | AVG | 585.4 | 38 | SH |
| 1297.2 | 38 | SH | 567.1 | 34 | AVG |
| 1255.8 | 24 | AVG | 523.7 | 35 | AVG |
| 1214.3 | 17 | AVG | 447.5 | 39 | AVG |
| 1090.8 | 10 | AVG | | | |
| 1070.6 | 7 | AVG | | | |

Band Freq.: Band Frequencies in Wavenumbers (cm−1)
Inten.: Intensity in percent transmittance (%T)
Data Type in Local Peak Region: BRD—Broad; AVG—Average; SHP—Sharp; SH—Shoulder
Peak List Edited. *Indicates peaks added.

| 25 Strongest Peaks | | | |
|---|---|---|---|
| %T | Freq. | %T | Freq. |
| 6 | 1685.0 | 32 | 1384.0 |
| 7 | 1070.5 | 34 | 567.0 |
| 10 | 1090.7 | 35 | 1605.8 |
| 10 | 1055.0 | 35 | 1423.5 |
| 12 | 3387.3 | 35 | 992.3 |
| 17 | 1647.3 | 35 | 523.6 |
| 17 | 1214.2 | 36 | 2879.0 |
| 24 | 1255.7 | 36 | 973.1 |
| 25 | 3114.3 | 37 | 1576.0 |
| 26 | 2962.0 | 37 | 634.5 |
| 26 | 2931.0 | 38 | 2863.5 |
| 31 | 1463.0 | 38 | 1297.1 |
| 31 | 889.1 | | |

Prep: KBR Pellet
Max %T: 101 @ 405.0
%T at 4000 (cm−1): 76
Density (cm−1/pt): 0.964

2. UV Absorption Spectrum [λmax (a)]

In water at:
pH 2.0, 261 (11.5)
pH 7.0, 262 (10.7)
pH 11.0, 262 (11.5)

3. Elemental Composition

Molecular formula: $C_{26}H_{42}N_4O_{13}$ SCIP. Molecular Weight, 716. Calcd C, 43.57; H, 5.86; N, 7.82; O, 29.05; S, 4.46; Cl, 4.89; P, 4.33.

4. Optical Rotation $[\alpha]_D^{25} + 105°$ (C, 0.94, water)

5. Solubilities

Highly soluble in water, methanol and ethanol. Slightly soluble in acetone and other ketones, ethyl acetate and other esters, chloroform and methylene chloride. Insoluble in saturated hydrocarbon solvents.

6. Antibacterial Activity

U-57930 3-(5′-uridylate) is not active in vitro. However, treatment with alkaline phosphatase or phosphodiesterase I yields U-57930 which is highly active against a variety of G+ organisms both in vitro and in vivo.

7. Melting Point: 202°–203° (with decomposition)

CHARACTERIZATION OF U-57930 3-(5′-GUANYLATE)

1. Tables listing the IR absorptions (Nujol and KBr) are as follows:

| Band Freq. | Inten. | Type | Band Freq. | Inten. | Type |
|---|---|---|---|---|---|
| 3335.3 | 16 | BRD | 1250.0 | 36 | SH |
| 3227.2 | 19 | BRD | 1213.3 | 21 | AVG |
| 2953.3 | 2 | AVG M | 1173.8 | 39 | AVG |
| 2925.3 | 1 | BRD M | 1149.7 | 41 | AVG |
| 2868.4 | 6 | SH M | 1087.9 | 14 | SH |
| 2855.9 | 4 | AVG M | 1071.5 | 9 | AVG |
| 2737.3 | 51 | BRD M | 991.5 | 42 | AVG |
| 2521.2 | 73 | BRD | 972.2 | 42 | AVG |
| 1684.0 | 6 | AVG | 956.8 | 52 | SH |
| 1635.8 | 11 | AVG | 929.8 | 51 | AVG |
| 1598.2 | 21 | AVG | 890.2 | 36 | AVG |
| 1572.1 | 26 | AVG | 860.3 | 51 | AVG |
| 1534.5 | 34 | AVG | 800.5 | 46 | AVG |
| 1462.2 | 18 | AVG M | 783.1 | 42 | SHP |
| 1414.9 | 44 | AVG | 720.4 | 43 | AVG M |
| 1377.3 | 24 | AVG M | 707.9 | 45 | BRD |

-continued

| Band Freq. | Inten. | Type | Band Freq. | Inten. | Type |
|---|---|---|---|---|---|
| 1365.7 | 31 | AVG | 681.9 | 40 | AVG |
| 1312.7 | 44 | AVG | 635.6 | 34 | AVG |

Band Freq.: Band Frequencies in Wavenumbers (cm−1)
Inten.: Intensity in Percent Transmittance (%T)
Data Type in Local Peak Region: BRD—Broad; AVG—Average; SHP—Sharp; SH—Shoulder
Peak List Edited. *Indicates Peaks Added.
M: Possible interference from Mineral Oil

| 25 Strongest Peaks | | | |
|---|---|---|---|
| %T | Freq. | %T | Freq. |
| 1 | 2925.2 | 24 | 1377.2 |
| 2 | 2953.2 | 26 | 1572.0 |
| 4 | 2855.8 | 31 | 1365.6 |
| 6 | 2868.3 | 34 | 1534.5 |
| 6 | 1684.0 | 34 | 635.5 |
| 9 | 1071.5 | 36 | 1250.0 |
| 11 | 1635.7 | 36 | 890.1 |
| 14 | 1087.8 | 39 | 1173.7 |
| 16 | 3335.2 | 40 | 681.8 |
| 18 | 1462.1 | 41 | 1149.6 |
| 19 | 3227.1 | 42 | 991.5 |
| 21 | 1598.1 | 42 | 972.1 |
| 21 | 1213.2 | | |

Prep: Mineral Oil Mull
Max %T: 97 @ 3762.6
%T at 3800 (cm−1): 97
Density (cm−1/pt): 0.964

| Band Freq. | Inten. | Type | Band Freq. | Inten. | Type |
|---|---|---|---|---|---|
| 3380.6 | 9 | BRD | 1174.7 | 31 | AVG |
| 3234.0 | 13 | BRD | 1147.7 | 33 | BRD |
| 2963.0 | 22 | AVG | 1088.9 | 9 | BRD |
| 2929.2 | 21 | BRD | 1070.6 | 6 | AVG |
| 2878.1 | 31 | AVG | 991.5 | 33 | AVG |
| 2862.7 | 33 | SH | 972.2 | 34 | AVG |
| 2274.0 | 44 | BRD | 956.8 | 43 | SH |
| 2522.2 | 61 | BRD | 929.8 | 44 | AVG |
| 1683.0 | 4 | BRD | 889.2 | 28 | AVG |
| 1634.8 | 6 | AVG | 860.3 | 41 | AVG |
| 1598.2 | 14 | AVG | 800.5 | 36 | AVG |
| 1571.2 | 19 | AVG | 783.1 | 32 | AVG |
| 1534.5 | 26 | AVG | 715.6 | 38 | SH |
| 1482.4 | 38 | AVG | 705.0 | 38 | SH |
| 1461.2 | 36 | AVG | 679.9 | 33 | AVG |
| 1448.7 | 36 | BRD | 635.6 | 31 | AVG |
| 1413.9 | 34 | AVG | 584.5 | 34 | SH |
| 1384.0 | 29 | AVG | 571.9 | 32 | AVG |
| 1359.9 | 30 | AVG | 523.7 | 31 | AVG |
| 1312.7 | 37 | AVG | 502.5 | 30 | AVG |
| 1250.9 | 29 | SH | 447.5 | 34 | AVG |
| 1213.3 | 16 | AVG | | | |

Band Freq.: Band Frequencies in Wavenumbers (cm−1)
Inten.: Intensity in Percent Transmittance (%T)
Data Type in Local Peak Region: BRD—Broad; AVG—Average; SHP—Sharp; SH—Shoulder
Peak List Edited. *Indicates Peaks Added.

| 25 Strongest Peaks | | | |
|---|---|---|---|
| %T | Freq. | %T | Freq. |
| 4 | 1683.0 | 29 | 1384.0 |
| 6 | 1634.7 | 29 | 1250.8 |
| 6 | 1070.5 | 30 | 1359.8 |
| 9 | 3380.5 | 30 | 502.5 |
| 9 | 1088.8 | 31 | 2878.0 |
| 13 | 3234.0 | 31 | 1174.6 |
| 14 | 1598.1 | 31 | 635.5 |
| 16 | 1213.2 | 31 | 523.6 |
| 19 | 1571.1 | 32 | 783.0 |
| 21 | 2929.1 | 32 | 571.8 |
| 22 | 2963.0 | 33 | 2862.6 |
| 26 | 1534.5 | 33 | 1147.6 |
| 28 | 889.1 | | |

Prep: KBR Pellet
Max %T: 97 @ 405.0
%T at 4000 (cm−1): 77
Density (cm−1/pt): 0.964

2. UV Absorption Spectrum [λmax (a)]

In water at:
pH 2.0, 256 (13.4); 280 (8.4) sh
pH 7.0, 254 (14.5); 273 (9.7) sh
pH 11.0, 259 (12.6); 266 (12.4) sh 3. Elemental Composition Molecular formula: $C_{27}H_{43}N_7O_{11}$ SCIP. Molecular Weight 739. Calcd C, 43.84; H, 5.81; N, 13.26; O, 23.27; S, 4.33; Cl, 4.73; P, 4.19. Found N, 13.32; S, 4.86; Cl, 4.49; P, 3.25.

4. Optical Rotation $[\alpha]_D^{25}, +97°$ (C, 0.855, water)

5. Solubilities

Highly soluble in water, methanol and ethanol. Slightly soluble in acetone and other ketones, ethyl acetate and other estes, chloroform and methylene chloride. Insoluble in saturated hydrocarbon solvents.

6. Antibacterial Activity

U-57930 3-(5′-guanylate) is not active in vitro. However, treatment with alkaline phosphatase or phosphodiesterase I yields U-57930 which is highly active against a variety of G+ organisms both in vitro and in vivo.

7. Melting Point: 219°–220° (with decomposition)

Since the compounds of the subject invention are amphoteric substances, they can form salts with both acids and bases by using standard procedures. Examples of inorganic acids which can be used to form salts are hydrochloric, sulfuric, phosphoric, and the like. Examples of inorganic bases are sodium, potassium, calcium, lithium, and the like. Salts of the compounds can be used for the same purposes as the parent compounds.

The following examples are illustrative of the best mode contemplated by the inventor for carrying out his invention and are not to be construed as limiting.

The examples use the 3-(5′-ribonucleotides) of U-57,930E or U-60,970E as the active compound and the malarial parasite as the protozoan, but it should be understood that this is only exemplary of the other active compounds of the subject invention in their use as antimalarials and, generally, as antiprotozoans. U-60,970E is the 4-cis-n-butyl-L-pipecolic acid amide of 7-Cl-methylthiolincosaminide. Its preparation is shown in Example 7 of U.S. patent application Ser. No. 148,056.

Reference hereinafter to U-57,930E or U-60,970E means the 3-(5'-ribonucleotide) of these compounds. The 3-ribonucleotides are those as disclosed herein.

EXAMPLE 1

Capsules

One thousand two-piece hard gelatin capsules for oral use, each containing 250 mg of U-57,930E or U-60,970E, are prepared from the following types and amounts of materials:

| U-57,930E or U-60,970E | 250 gm |
|---|---|
| Corn starch | 100 gm |
| Talc | 75 gm |
| Magnesium stearate | 25 gm |

The materials are thoroughly mixed and then encapsulated in the usual manner.

The foregoing capsules are useful for the treatment of malaria in adult humans by oral administration of one capsule every 6 hours.

Using the procedure above, capsules are similarly prepared containing U-57,930E or U-60,970E in 10, 25, 50, 100, and 500 mg amounts by substituting 10, 25, 50, 100 and 500 gm of U-57,930E or U-60,970E for the 250 gm used above.

EXAMPLE 2

Capsules

One thousand two-piece hard gelatin capsules for oral use, each containing 200 mg. of U-57,930E or U-60,970E and 200 mg of hydroxychloroquine sulfate, are prepared from the following types and amounts of ingredients:

| U-57,930E or U-60,970E | 200 gm |
|---|---|
| Hydroxychloroquine sulfate | 200 gm |
| Talc | 75 gm |
| Magnesium stearate | 25 gm |

The ingredients are thoroughly mixed and then encapsulated in the usual manner.

The foregoing capsules are useful to prevent recurrent attacks of *P. vivax.* in adult humans by the oral administration of 1 capsule weekly.

EXAMPLE 3

Tablets

One thousand tablets for oral use, each containing 500 mg of U-57,930E or U-60,970E, are prepared from the following types and amounts of materials:

| U-57,930E or U-60,970E | 500 gm |
|---|---|
| Lactose | 125 gm |
| Corn starch | 65 gm |
| Magnesium stearate | 25 gm |
| Light liquid petrolatum | 3 gm |

The ingredients are thoroughly mixed and slugged. The slugs are broken down by forcing through a number 16 screen. The resulting granules are then compressed into tablets, each tablet containing 500 mg of U-57,930E or U-60,970E.

The foregoing tablets are useful for treatment of malarial infections in adult humans by oral administration of one tablet three times a day.

Using the above procedure, except for reducing the amount of U-57,930E or U-60,970E to 250 gm, tablets containing 250 mg of U-57,930E or U-60,970E are prepared.

EXAMPLE 4

Tablets

One thousand oral tablets, each containing 125 mg of U-57,930E or U-60,970E and 325 mg of quinine sulfate, are prepared from the following types and amounts of materials:

| U-57,930E or U-60,970E | 125 gm |
|---|---|
| Quinine sulfate | 325 gm |
| Lactose | 50 gm |
| Corn starch | 50 gm |
| Calcium stearate | 25 gm |
| Light liquid petrolatum | 5 gm |

The ingredients are thoroughly mixed and slugged. The slugs are broken down by forcing through a number 16 screen. The resulting granules are then compressed into tablets, each containing 125 mg of U-57,930E or U-60,970E and 325 mg of quinine sulfate.

The foregoing tablets are useful for treatment of malaria by the oral administration of two tablets every 8 hours for 7 days, then one tablet three times a day for 7 days.

EXAMPLE 5

Oral Syrup

One thousand cc of an aqueous suspension for oral use, containing in each 10 cc dose 25 mg of pyrimethamine, 250 mg of U-57,930E or U-60,970E and 500 mg of sulfadiazine is prepared from the following types and amounts of ingredients:

| U-57,930E or U-60,970E | 25 gm |
|---|---|
| Pyrimethamine | 2.5 gm |
| Sulfadiazine | 50 gm |
| Citric acid | 2 gm |
| Benzoic acid | 1 gm |
| Sucrose | 700 gm |
| Tragacanth | 5 gm |
| Lemon oil | 2 cc |
| Deionized water, q.s. | 1000 cc |

The citric acid, benzoic acid, sucrose, tragacanth, and lemon oil are dispersed in sufficient water to make 850 cc of solution. The U-57,930E or U-60,970E pyrimethamine and sulfadiazine are stirred into the syrup until uniformly distributed. Sufficient water is added to make 1000 cc.

The composition so prepared is useful in the prophylactic treatment of malaria in adult humans at a dose of 1 tablespoonful (10 cc) weekly.

EXAMPLE 6

PARENTERAL SOLUTION

A sterile aqueous solution for intramuscular use, containing 200 mg of U-57,930E or U-970E in 1 cc is prepared from the following types and amounts of materials:

| | |
|---|---|
| U-57,930E or U-60,970E | 200 gm |
| Lidocaine hydrochloride | 4 gm |
| Methylparaben | 2.5 gm |
| Propylparaben | 0.17 gm |
| Water for injection, q.s. | 1,000 cc |

The ingredients are dissolved in the water and the solution sterilized by filtration. The sterile solution is filled into vials and the vials sealed.

EXAMPLE 7

PARENTERAL PREPARATION

A sterile aqueous composition for intramuscular use, containing in 1 cc 200 mg of U-57,930E or U-60,970E is prepared from the following types and amounts of ingredients:

| | |
|---|---|
| U-57,930E or U-60,970E | 200 gm |
| Lactose | 50 gm |
| Water for injection, q.s. | 1,000 cc |

The U-57,930E or U-60,970E and lactose are dispersed in the water and sterilized. The sterile composition, in the amount of 2 cc, is filled aseptically into sterile vials.

EXAMPLE 8

Following the procedure of each of the preceding Examples 1-7, inclusive, each antimalarially-active compound of the subject invention is substituted in an equivalent amount for the U-57,930E or U-60,970E shown in the example to provide therapeutic properties. Similarly, each of the above compounds can be used in the form of a pharmaceutically (or pharmacologically) acceptable salt, e.g., hydrochloride, sulfate, phosphoric, sodium, potassium, calcium, and lithium.

Test results showing the antimalarial efficacy of U-57,930E in comparison with clindamycin HCl (U-21,251F), 4'-pentyl 1'-N-demethyl clindamycin (U-24,729A) and chloroquine (U-8,284) are as follows:

| | In Vivo Results vs. P. berghei | | | |
|---|---|---|---|---|
| | MED[1] (mg/kg) | | $CD_{50}$[2] (mg/kg) | |
| COMPOUND | Sub. Q[3] | OI | Sub Q | OI |
| U-57,930E | 0.16 | 1.6 | 16 (12–22) | >50 |
| U-21,251F | <20 | — | 53 (46–61) | — |
| U-24,729A | <1.25 | — | 4.7 (3.2–6.9) | — |
| U-8,284 Chloroquine | <5–10 | 12.5 | 11.5 (8.8–15) | 14 |
| Chloroquine $(PO_4)_2$ | <5 | — | >20 | — |

[1]MED = Dosage at which median survival time ($ST_{50}$) was increased significantly (p = 0.05) over $ST_{50}$ of untreated controls.
[2]$CD_{50}$ = Median protective dose in mg/kg 95% limits.
[3]Route of administration

Anti-Malarial Test (P. berghei)

Test method. Male, CF-1 mice (18 to 20 g) were housed in groups of 10 and were infected intraperitoneally with whole blood from mice infected with P. berghei 3 days prior to bleeding. A 0.2-ml amount of heparinized blood, diluted 1:10 with saline, served as the inoculum. This volume contained approximately $10^6$ parasites.

At 4 hr postinfection, each group of 10 mice was treated, either subcutaneously with 0.2 ml or orally by gavage, with 0.5 ml of the desired drug concentration. Treatment was continued once each day for 4 days. The animals were observed for 28 days and deaths were recorded. Deaths prior to the 6th day were considered traumatic.

Evaluation for efficacy of the various analogues and drug concentrations of individual analogues was based on the median survival time of animals at each treatment level and the median protective dose of the individual analogue. Calculations were computed on an IBM 370 digital computer. Results based on the treated groups were compared with those of untreated groups or groups treated with chloroquine.

Other protozoans within the concept of the subject invention process are intracellular parasites, for example, the species of Plasmodia, Toxoplasma, and Leishmania; protozoa that digest the red blood cells (RBC's) of treated patients, for example, Entamoeba histolytica and certain Trypanosoma; and other helminths which injest RBC's during the disease processes, for example, the Schistosomes.

CHART 1

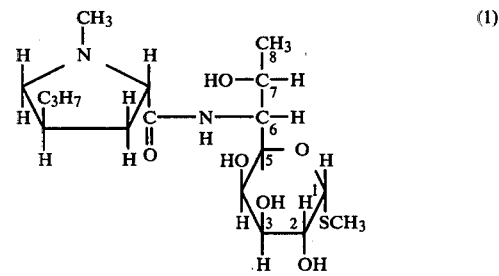

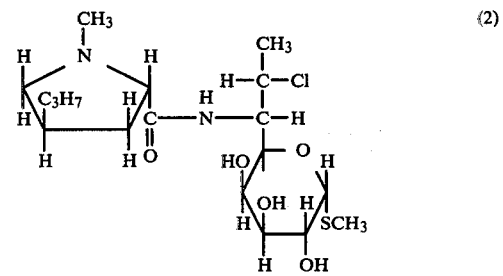

CHART 2

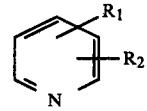

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substitued phenyl, —$(CH_2)_n$—OH, —$(CH_2)_n$—$NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof; wherein $R_2$, which can be singly substituted in any position of the pyridine ring not already substituted by $R_1$, is

and X is the amino function of a compound selected from the group 7(R)-hydroxy-methyl 1-thio-α-lincosaminide, 7(S)-hydroxy-methyl 1-thio-α-lincosaminide, 7(S)-halo-methyl 1-thio-α-lincosaminide, 7(R)-halo-methyl 1-thio-α-lincosaminide, 7(S)-methoxymethyl 1-thio-α-lincosaminide, 7-deoxy-7(S)-(methylthio)-methyl 1-thio-α-lincosaminide, 7-deoxy-7(S)-(2-hydroxyethylthio)-methyl 1-thio-α-lincosaminide and 7-deoxy-7(S)-(3-hydroxypropylthio)-methyl 1-thio-α-lincosaminide; and the pharmaceutically acceptable salts thereof.

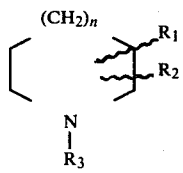

wherein $R_1$ and $R_2$, which can be in the 2, 3, 4, 5, 6, 7, 8, or 9 position of the ring, are as defined above; wherein $R_3$ is selected from the group consisting of H, $CH_3$, $C_2H_5$, and $-CH_2-CH_2-OH$; wherein n is an integer of from 1 to 4, inclusive, and the pharmaceutically acceptable salts thereof.

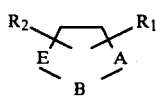

wherein A, B and E are selected from the group consisting of nitrogen, oxygen, sulfur and $CR_1R_1$; $R_1$ and $R_2$ are as defined above, and can be attached to any ring carbon or nitrogen atom; $R_1$ can be multiply attached to any ring carbon atom, and the pharmaceutically acceptable salts thereof.

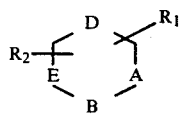

wherein A, B, D and E are selected from the group consisting of nitrogen, oxygen, sulfur and $CR_1R_1$; $R_1$ and $R_2$ are as defined above and can be attached to any ring carbon or nitrogen atom; $R_1$ can be multiply attached to any ring carbon atom, and the pharmaceutically acceptable salts thereof.

CHART 3

-continued
CHART 3

1: R = H
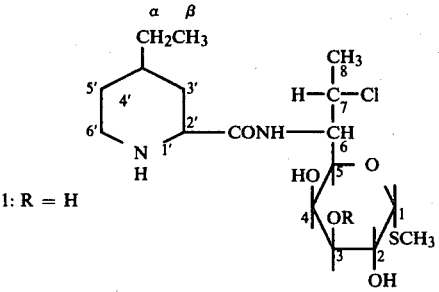

2: R = 
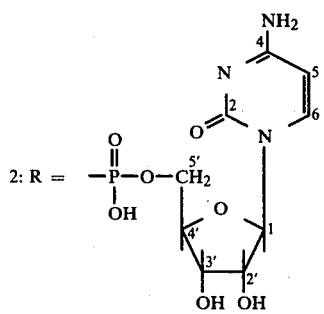

3: R = 
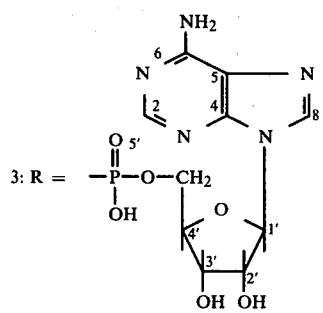

4: R = 
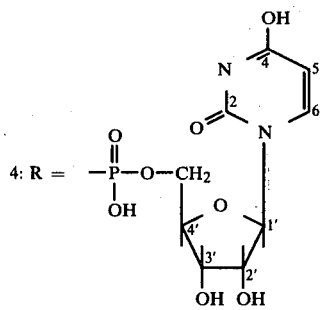

5: R = 
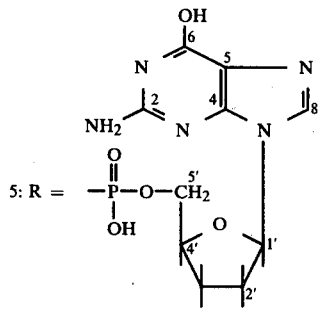

-continued
CHART 3

1: U-57930
2: U-57930 3-(5'-cytidylate)
3: U-57930 3-(5'-adenylate)
4: U-57930 3-(5'-uridylate)
5: U-57930 3-(5'-guanylate)

We claim:

1. A process for treating malaria comprising the administration of an effective antimalarial amount of the 3-(5'-ribonucleotide) of a compound having the formula

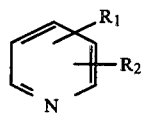

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof; wherein $R_2$, which can be singly substituted in any position of the pyridine ring not already substituted by $R_1$, is

and X is the amino function of a compound selected from the group consisting of 7(S)-halo-methyl 1-thio-α-lincosaminide and 7(R)-halo-methyl 1-thio-α-lincosaminide; or the pharmaceutically acceptable salts thereof, to a mammal hosting a malarial parasite.

2. A process for treating malaria comprising the administration of an effective antimalarial amount of the 3-(5'-ribonucleotide) of a compound having the formula

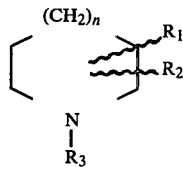

wherein $R_1$ and $R_2$, which can be in the 2, 3, 4, 5, 6, 7, 8, or 9 position of the ring, are as defined in claim 1; wherein $R_3$ is selected from the group consisting of H, $CH_3$, $C_2H_5$, and $-CH_2-CH_2-OH$; wherein n is an integer of from 1 to 4, inclusive; or the pharmaceutically acceptable salts thereof, to a mammal hosting a malarial parasite.

3. A process for treating malaria comprising the administration of an effective antimalarial amount of a compound, as defined in claim 1, wherein $R_1$ is in the 4 position and is alkyl of from 1 to 8 carbon atoms, inclusive, and isomeric forms thereof; wherein $R_2$ is in the 2 or 3 position; or the pharmaceutically acceptable salts thereof, to a mammal hosting a malarial parasite.

4. A process for treating malaria comprising the administration of an effective antimalarial amount of a compound, as defined in claim 2, wherein $R_1$ is in the 4 position and is alkyl of from 1 to 8 carbon atoms, inclusive, and isomeric forms thereof; or the pharmaceutically acceptable salts thereof, to a mammal hosting a malarial parasite.

5. A process for treating malaria comprising the administration of an effective antimalarial amount of the 3-(5'-ribonucleotide) of a compound having the formula

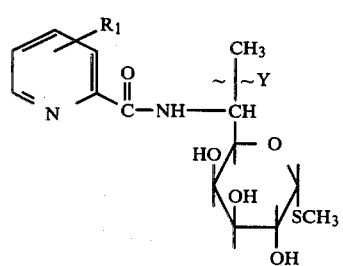

wherein $R_1$, which can be singly or multiply substituted in the 3, 4, 5, or 6 position of the pyridine ring, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and isomeric forms thereof, wherein n is an integer of from 1 to 8, inclusive, $R_4$ and $R_5$ are H or alkyl or from 1 to 8 carbon atoms, inclusive, and isomeric forms thereof; wherein Y is selected from the group consisting of 7(S)-halo or 7(R)-halo; and the pharmaceutically acceptable salts thereof, to a mammal hosting a malarial parasite.

6. A process for treating malaria comprising the administration of an effective antimalarial amount of a compound, as defined in claim 5, wherein Y is 7(S)-halo, or the pharmaceutically acceptable salts thereof, to a mammal hosting a malarial parasite.

7. A process for treating malaria comprising the administration of an effective antimalarial amount of the 3-(5'-ribonucleotide) of a compound having the formula

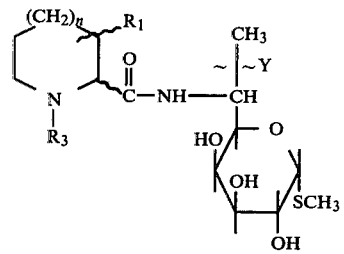

wherein $R_1$, which can be singly or multiply substituted in the 3, 4, 5, 7, 8 or 9 position of the ring, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, —(CH$_2$)$_n$—OH, —(CH$_2$)$_n$—NR$_4$R$_5$, and isomeric forms thereof, wherein n is an integer of from 1 to 8, inclusive, R$_4$ and R$_5$ are H or alkyl or from 1 to 8 carbon atoms, inclusive, and isomeric forms thereof; wherein R$_3$ is selected from the group consisting of H, CH$_3$, C$_2$H$_5$, and —CH$_2$—CH$_2$—OH; wherein n is an integer of from 1 to 4, inclusive, wherein Y is selected from the group consisting of 7(S)-halo and 7(R)-halo; or the pharmaceutically acceptable salts thereof, to a mammal hosting a malarial parasite.

8. A process, according to claim 7, wherein 7(S)-halo is 7(S)-chloro.

9. A process for treating malaria comprising the administration of an effective antimalarial amount of a compound as defined in claim 7 wherein Y is 7(S)-halo; R$_1$ is alkyl of from 1 to 8 carbon atoms, inclusive, and isomeric forms thereof; R$_3$ is hydrogen, or the pharmaceutically acceptable salts thereof, to a mammal hosting a malarial parasite.

10. A process, as defined in claim 9, wherein the compound used is as follows: Y is 7(S)-halo; R$_1$ is C$_2$H$_5$ and R$_3$ is hydrogen.

11. A process, as defined in claim 9, wherein the compound used is as follows; Y is 7(S)-halo; R$_1$ is C$_4$H$_9$ and R$_3$ is hydrogen.

12. A process, as defined in claim 9, wherein the 7(S)-halo of the compound used is 7(S)-chloro.

13. A process, as defined in claim 10, wherein the 7(S)-halo of the compound used is 7(S)-chloro.

14. A process, as defined in claim 11, wherein the 7(S)-halo of the compound used is 7(S)-chloro.

15. The process of claim 7 wherein from about 0.5 to about 300 mg of compound per kg of host body weight is administered daily in association with a pharmaceutical carrier.

16. The process of claim 7 wherein from about 0.5 to about 200 mg of compound per kg of host body weight is parenterally administered daily in association with a sterile pharmaceutical carrier.

17. The process of claim 7 wherein from about 1 to about 300 mg of compound per kg of host body weight is orally administered daily in association with a pharmaceutical carrier.

18. A process for treating malaria comprising the administration of an effective antimalarial amount of the 3-(5'-ribonucleotide) of a compound having the formula

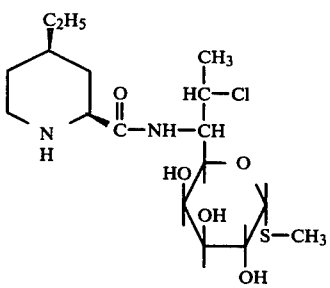

or the pharmaceutically acceptable salts thereof, to a mammal hosting a malarial parasite.

19. The process of claim 18 wherein from about 0.5 to about 300 mg of compound per kg of host body weight is administered daily in association with a pharmaceutical carrier.

20. The process of claim 18 wherein from about 0.5 to about 200 mg of compound per kg of host body weight is parenterally administered daily in association with a sterile pharmaceutical carrier.

21. The process of claim 18 wherein from about 1 to about 300 mg of compound per kg of host body weight is orally administered daily in association with a pharmaceutical carrier.

22. A process for treating malaria comprising the administration of an effective antimalarial amount of the 3-(5'-ribonucleotide) of a compound having the formula

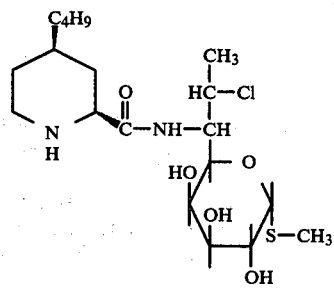

or the pharmaceutically acceptable salts thereof, to a mammal hosting a malarial parasite.

23. The process of claim 22 wherein from about 0.5 to about 300 mg of compound per kg of host body weight is administered daily in association with a pharmaceutical carrier.

24. The process of claim 22 wherein from about 0.5 to about 200 mg of compound per kg of host body weight is parenterally administered daily in association with a sterile pharmaceutical carrier.

25. The process of claim 22 wherein from about 1 to about 300 mg of compound per kg of host body weight is orally administered daily in association with a pharmaceutical carrier.

26. A process for treating malaria comprising the administration of an effective antimalarial amount of the 3-(5'-ribonucleotide) of a compound having the formula

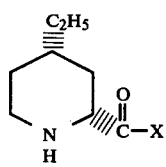

wherein X is selected from the group consisting of 7(S)-halo-methyl 1-thio-α-lincosaminide and 7(R)-halo-methyl 1-thio-α-lincosaminide; or the pharmaceutically acceptable salts thereof, to a mammal hosting a malarial parasite.

27. A process for treating malaria comprising the administration of an effective antimalarial amount of the 3-(5'-ribonucleotide) of a compound having the formula

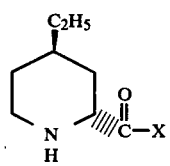

wherein X is as defined in claim 26, or the pharmaceutically acceptable salts thereof, to a mammal hosting a malarial parasite.

28. A process for treating malaria comprising the administration of an effective antimalarial amount of the 3-(5'-ribonucleotide) of a compound having the formula

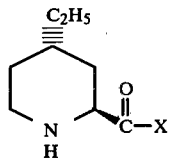

wherein X is as defined in claim 26, or the pharmaceutically acceptable salts thereof, to a mammal hosting a malarial parasite.

29. A process for treating a protozoan infection comprising the administration of an effective antiprotozoan amount of the 3-(5'-ribonucleotide) of a compound having the formula

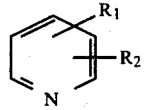

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof; wherein $R_2$, which can be singly substituted in any position of the pyridine ring not already substituted by $R_1$, is

and X is the amino function of a compound selected from the group consisting of 7(S)-halo-methyl 1-thio-α-lincosaminide and 7(R)-halo-methyl 1-thio-α-lincosamoinide; or the pharmaceutically acceptable salts thereof, to a mammal hosting a protozoan parasite.

30. A process for treating a protozoan infection comprising the administration of an effective antiprotozoan amount of the 3-(5'-ribonucleotide) of a compound having the formula

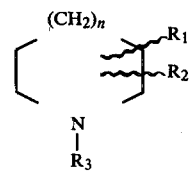

wherein $R_1$ and $R_2$, which can be in the 2, 3, 4, 5, 6, 7, 8, or 9, position of the ring, are as defined in claim 1; wherein $R_3$ is selected from the group consisting of H, $CH_3$, $C_2H_5$, and $-CH_2-CH_2-OH$; wherein n is an integer of from 1 to 4, inclusive; or the pharmaceutically acceptable salts thereof, to a mammal hosting a protozoan parasite.

31. A process, according to claim 30, wherein the 3-(5'-ribonucleotide) is selected from the group consisting of the 3-(5'-cytidylate), 3-(5'-adenylate), 3-(5'-uridylate), and 3-(5'-guanylate).

* * * * *